US00PP22926P2

(12) United States Plant Patent
Maas

(10) Patent No.: US PP22,926 P2
(45) Date of Patent: Aug. 7, 2012

(54) ***PHLOX* PLANT NAMED 'PARTY PUNCH'**

(50) Latin Name: *Phlox paniculata*
Varietal Denomination: Party Punch

(75) Inventor: Dick Maas, Hillegom (NL)

(73) Assignee: Plants Nouveau, LLC, Charleston, NC (US)

( * ) Notice: Subject to any disclaimer, the term of this patent is extended or adjusted under 35 U.S.C. 154(b) by 47 days.

(21) Appl. No.: 12/927,702

(22) Filed: Nov. 22, 2010

(51) Int. Cl.
*A01H 5/00* (2006.01)

(52) U.S. Cl. ..... Plt./320

(58) Field of Classification Search ..... Plt./320
See application file for complete search history.

(56) References Cited

OTHER PUBLICATIONS

Kuack. New Perennial Varieties. Greenhouse Management Aug. 2009, retrieved from the Internet at <http://www.greenhousemanagementonline.com/gm_0809_newvarieties.aspx> 11 pp.*

* cited by examiner

*Primary Examiner* — June Hwu
(74) *Attorney, Agent, or Firm* — Penny J. Aguirre

(57) ABSTRACT

A new and distinct cultivar of *Phlox* plant named 'Party Punch', characterized by its compact and upright plant habit, its strong stems, its grass green leaves, its medium sized and long lasting pinkish-orange colored flowers, and its resistance to powdery mildew.

2 Drawing Sheets

Botanical classification: *Phlox paniculata.*
Cultivar designation: 'Party Punch'.

BACKGROUND OF THE INVENTION

The present invention relates to a new and distinct cultivar of *Phlox* plant, botanically known as *Phlox paniculata* 'Party Punch' and will be referred to hereafter by its cultivar name, 'Party Punch'. The new cultivar represents a new herbaceous perennial grown for landscape use.

The new cultivar of *Phlox* was discovered as a naturally occurring whole plant mutation by the Inventor in a field planted with numerous cultivars of *Phlox paniculata* in Hillegom, The Netherlands in July 2005. The parentage is unknown.

Asexual reproduction of the new cultivar was first accomplished by stem cuttings in Hillegom, The Netherlands in 2005 by the Inventor. It has been determined that the characteristics of this cultivar are stable and are reproduced true to type in successive generations.

SUMMARY OF THE INVENTION

The following traits have been repeatedly observed and are determined to be the unique characteristics of 'Party Punch'. These characteristics in combination distinguish 'Party Punch' as a new and distinct cultivar of *Phlox.*

1. 'Party Punch' exhibits a compact and upright plant habit.
2. 'Party Punch' exhibits strong stems.
3. 'Party Punch' exhibits clear, medium green-colored stems and leaves.
4. 'Party Punch' exhibits pinkish-orange colored flowers.
5. 'Party Punch' exhibits a very high degree of resistance to powdery mildew.

Plants of the new *Phlox* can be compared to plants of *Phlox paniculata* 'Orange Perfection', (un-patented). Plants of the new *Phlox* and 'Orange Perfection' differ primarily in the following characteristics: 1. Plants of the new *Phlox* have a shorter plant habit than plants of 'Orange Perfection' 2. Flowers of plants of the new *Phlox* are more pink in color than flowers of plants of 'Orange Perfection'. 3. Plants of the new *Phlox* are more resistant to powdery mildew than plants of 'Orange Perfection'.

Plants of the new *Phlox* can also be compared to plants of *Phlox paniculata* 'Bartwelve' (U.S. Plant Pat. No. 11,804). Plants of the new *Phlox* and 'Bartwelve' differ primarily in the following characteristics: 1. Plants of the new *Phlox* have a bushier habit than plants of 'Bartwelve'. 2. Flowers of plants of the new *Phlox* are more orange in color and have a white eye instead of the deep pink eye observed on plants of 'Bartwelve'. 3. Plants of the new *Phlox* are much more resistant to powdery mildew than plants of 'Bartwelve'.

BRIEF DESCRIPTION OF THE DRAWING

The accompanying colored photographs illustrate the overall appearance and distinct characteristics of the new *Phlox*. The photographs were taken of a three year-old plant of 'Party Punch' as grown in a garden in Baltimore, Md.

The photograph in FIG. 1 comprises a side perspective view of a typical plant of 'Party Punch'.

Figure 1:
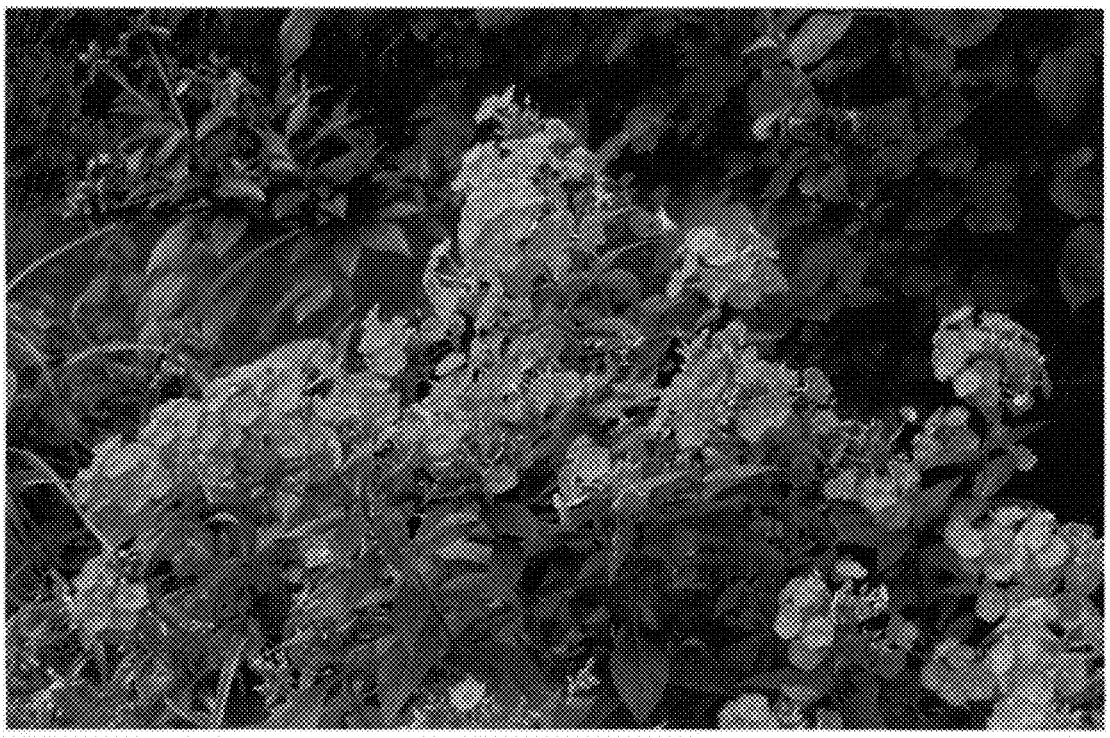
Figure 2:
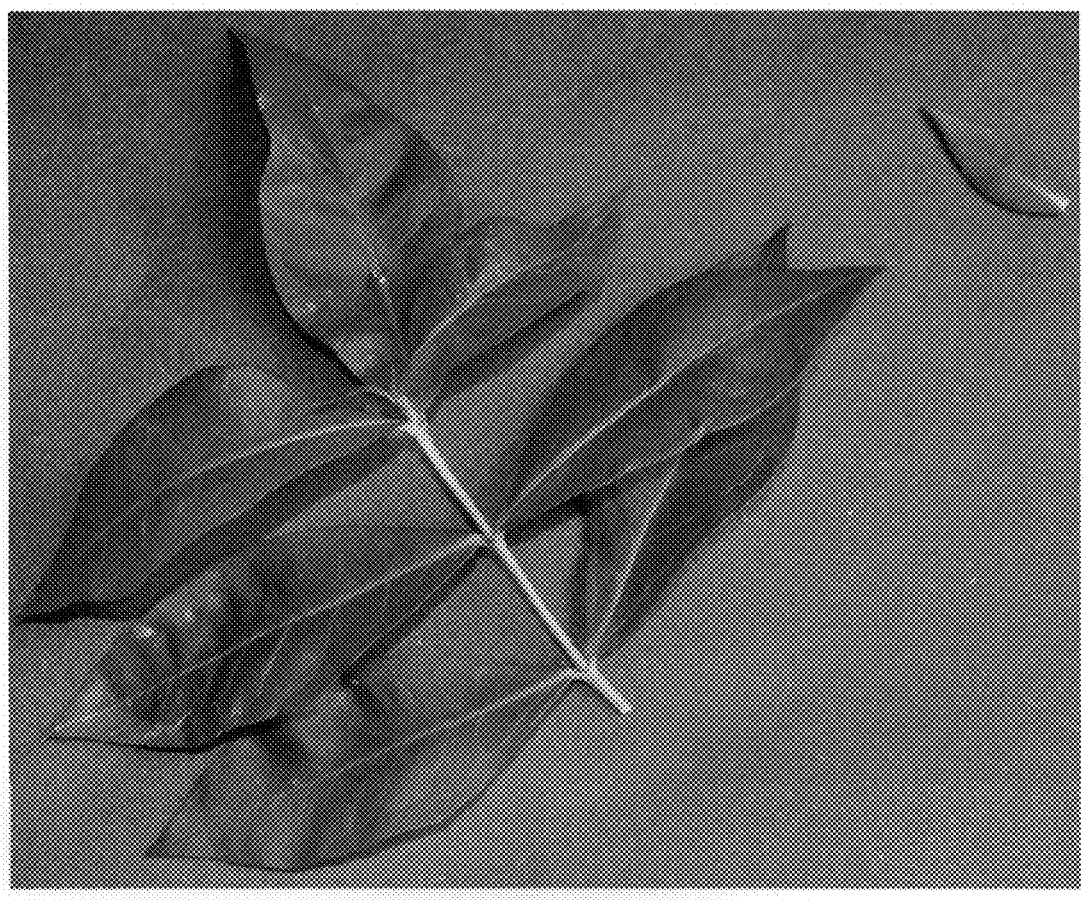

The photograph in FIG. 2 provides a close-up view of typical leaves of 'Party Punch' with a developing leaf shown in the upper right.

Figure 3:
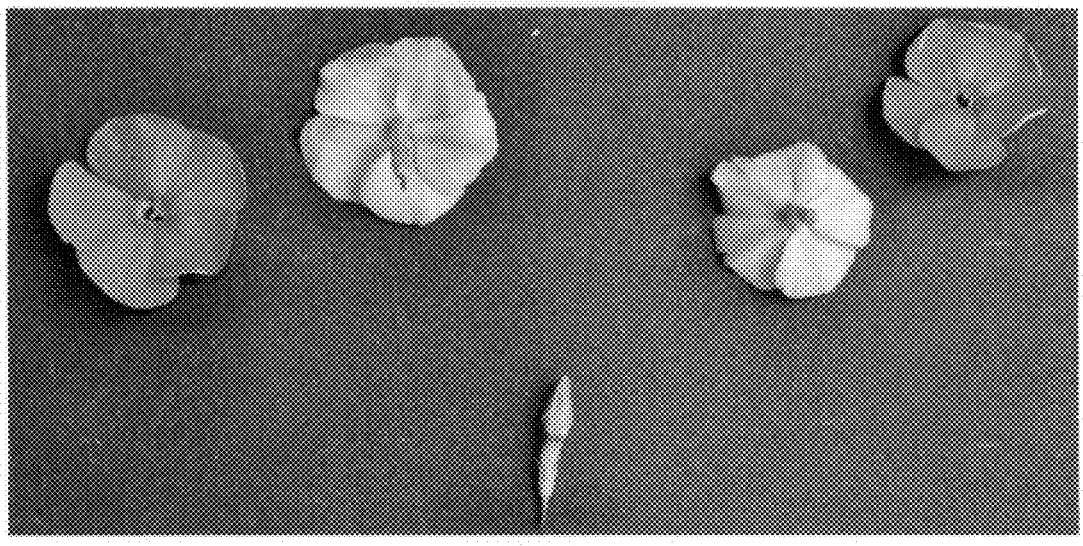

The photograph in FIG. 3 provides a close-up view of typical flowers and flower buds of 'Party Punch'; mature aging flowers are shown in the upper left (upper and lower surface), newly opened flowers are shown in the upper right (lower and upper surface), and a flower bud is shown in the lower center. The colors in the photograph may differ slightly from the color values cited in the detailed botanical description, which accurately describe the colors of the new *Phlox.*

DETAILED BOTANICAL DESCRIPTION OF THE PLANT

The following is a detailed description of three year-old plants of the new cultivar as grown outdoors in a garden in Baltimore, Md. The plants were grown under average day temperatures of 23° C. to 40° C. and average night temperatures of 15° C. to 32° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Continuously from June to September in Baltimore, Md.

*Plant habit*.—Herbaceous perennial, compact, upright.

*Height and spread*.—Reaches about 60 cm in height and about 50 cm in spread.

*Hardiness*.—Tolerant to temperatures ranging from −20° C. to 40° C.

*Environmental stresses*.—Good garden performance with tolerance to rain and wind.

*Diseases and pests*.—Has shown very good resistance to powdery mildew, no susceptibility or resistance to pests has been observed.

*Root description*.—Moderate branching, dense, fibrous.

Growth and propagation:

*Growth rate*.—Moderate.

*Propagation*.—Stem cuttings.

*Time to initiate roots*.—About two weeks at 15° C. to 25° C.

*Time to produce a rooted young plant*.—About 35 days at 15° C. to 25° C.

Stem description:

*Stem size*.—An average of 23 cm in length and 3 mm in width.

*Stem shape*.—Round.

*Stem strength*.—Strong and sturdy.

*Stem color*.—Close to 144A.

*Stem surface*.—Glabrous, smooth.

*Stem aspect*.—Held nearly upright.

*Internode length*.—An average of 2.8 cm.

*Branching habit*.—Flowering stems emerge from crown, an average of 5 stems per plant three years in age, pinching enhances branching.

Foliage description:

*Leaf shape*.—Narrowly ovate to elliptic.

*Leaf division*.—Simple.

*Leaf base*.—Obtuse.

*Leaf apex*.—Narrowly acute.

*Leaf venation*.—Pinnate.

*Leaf margins*.—Very finely serrate.

*Leaf attachment*.—Petiolate.

*Leaf arrangement*.—Opposite.

*Leaf size*.—An average of 10 cm in length and 4 cm in width.

*Leaf fragrance*.—None.

*Leaf surface*.—Smooth and glabrous on upper and lower surface.

*Leaf color*.—Developing leaves upper surface; about 137C with venation close to 144C, developing leaves lower surface; about 138B, fully expanded leaves upper surface; about 137A, venation close to 144C, fully expanded leaves lower surface; about 138B, venation close to 144C.

*Petioles*.—Length; about 2.5 mm, diameter; about 1.5 mm, texture on upper and lower surfaces; smooth, glabrous, color upper and lower surfaces; close to 144D.

Flower description:

*Inflorescence type*.—Compound terminal panicle of single rotate flowers, panicle rounded in shape.

*Lastingness of inflorescence*.—About 4 weeks from the opening of the first flower to senescence of last flower, individual flower lasts about 10 days, not persistent.

*Inflorescence size*.—An average of 9 cm in height and 10 cm in diameter.

*Flower fragrance*.—Moderate, sweet and flowery.

*Flower number*.—Average of 60 per inflorescence, one inflorescence per flowering stem.

*Flower aspect*.—Primarily outward.

*Flower bud*.—An average of 1.4 cm in length and up to 3 mm in width, narrow oblanceolate in shape, NN155B with blushing of 67B in color.

*Flower form*.—Explanate with tubular base.

*Flower size*.—An average of 2.8 cm in length and 3.4 cm in diameter.

*Corolla tube*.—About 1.5 cm in length, 3 mm in width, close to NN155B with striations of 67B in color on developing and mature flowers, smooth surface.

*Corolla lobes*.—5, roughly spatulate in shape, held horizontally when fully open, slightly overlapping, about 1.7 cm in length and 7 mm in width, apex rounded, base fused to tube, entire margins, color developing petals, upper surface; close to N66A; close to N57B towards the throat, developing petals, lower surface; 155B with striations of 58D, fully expanded petals, upper surface; close to N78A with spots, between 76D and N155A and towards the throat, darker than 67A, fully expanded petals, lower surface; NN155C with blushings of N57A and N78A, eye color; NN155B.

*Sepals*.—5, fused towards base, lanceolate in shape, margins entire, apex narrowly apiculate, an average of 7 mm in length and 1.7 mm in width, surface is smooth and glabrous on upper and lower surface, color on developing and fully developed flowers upper surface and lower surface; close to 143C, color of fully open flowers upper and lower surface; close to 142B.

*Peduncles*.—Length; about 5 cm, diameter; about 2 mm, strength; strong, texture; smooth, glabrous, close to 144A in color.

*Pedicels*.—Length: about 5 mm, diameter; about 1 mm, strength; strong, texture; smooth, glabrous, close to 144C in color.

Reproductive organs:

*Gynoecium*.—1 pistil, about 1.2 cm in length, stigma is three parted and close to 141C in color, style is about 3 mm in length and close to 141C in color, ovary is inferior and 141C in color.

*Androcoecium*.—Typically 5 stamens, anthers are basifixed, oblong in shape, 3 mm in length and 2D in color, filaments are about 5 mm in length, pollen is moderate in quantity and close to 11C in color.

*Fruit and seeds*.—Development has not been observed.

It is claimed:

1. A new and distinct cultivar of *Phlox* plant named 'Party Punch' as herein illustrated and described.

* * * * *